United States Patent [19]
Gross et al.

[11] 3,990,851
[45] Nov. 9, 1976

[54] PROCESS AND DEVICE FOR MEASURING ANTIGEN-ANTIBODY REACTIONS

[75] Inventors: Jurgen Gross, Hofheim, Taunus; Arno Holst; Helmut Lask, both of Wiesbaden; Axel Sieber, Marburg-Marbach, all of Germany

[73] Assignee: Behringwerke Aktiengesellschaft, Marburg an der Lahn, Germany

[22] Filed: Feb. 25, 1975

[21] Appl. No.: 552,883

[30] Foreign Application Priority Data
Feb. 27, 1974 Germany............................ 2409273

[52] U.S. Cl. .............................. 23/253 R; 23/230 B; 250/574; 356/103; 356/208; 424/12
[51] Int. Cl.².................... G01N 33/16; G01N 21/24
[58] Field of Search ...................... 23/230 B, 253 R; 250/574, 575; 356/103, 208; 424/12

[56] References Cited
UNITED STATES PATENTS

| | | | |
|---|---|---|---|
| 3,646,352 | 2/1972 | Bol et al. ....................... | 356/103 X |
| 3,786,261 | 1/1974 | Tucker............................ | 250/574 X |
| 3,830,569 | 8/1974 | Meric.............................. | 356/102 X |
| 3,835,315 | 9/1974 | Gravitt, Jr........................... | 250/574 |
| 3,843,268 | 10/1974 | Kaye................................ | 250/574 |

*Primary Examiner*—R.E. Serwin
*Attorney, Agent, or Firm*—Curtis, Morris & Safford

[57] ABSTRACT

Antigen-antibody reactions are measured by passing laser light through the mixture of the antigen solution with the corresponding antibody and measuring the light scattered in the forward direction and determining its intensity. The device used comprises a measuring system consisting of a laser, at least two diaphragms, a system of lenses and a photodetector and a light trap having a diameter corresponding to 1.1 to 1.7 times the diameter of the laser beam.

4 Claims, 3 Drawing Figures

PROCESS AND DEVICE FOR MEASURING ANTIGEN-ANTIBODY REACTIONS

This invention relates to a process for measuring antigen-antibody reactions by means of laser light and to a device to carry out said process.

Quantitative data about proteins in body fluids are a decisive characteristic of the examined organism.

Immunologic methods of determination of antigens are based on the property of the latter stoichiometrically to react with their specific antibodies with formation of precipitates. Based on this principle, a series of processes has been developed the most important of which are listed below in the order of increasing sensitivity with the possible limits of detection.

| | |
|---|---|
| double diffusion | 40 µg/ml |
| analysis of precipitate | 12.5 – 20 µg/ml |
| linear immune diffusion | 12.5 µg/ml |
| radical immune diffusion | 10 µg/ml |
| flocculation test | 1.3 – 3.0 µg/ml |
| ring test | 0.2 – 0.4 µg/ml |
| complement fixation reaction | 0.1 µg/ml |
| indirect hemagglutination | 0.02 – 0.04 µg/ml |
| hemagglutination inhibition test | 0.006 – 0.01 µg/ml |
| radio-immunologic assay | 0.00005 – 0.005 µg/ml |

The aforesaid summary shows that the diffusion method is often not sensitive enough for numerous antigens in body fluids or filtrates of cultures of microorganisms. Moreover, these methods are very time-consuming because of the required diffusion period. Whilst the more sensitive test methods, for example the hemagglutination, are rather complicated, the radio-immunologic assays require very expensive reagents and measuring devices.

A sensitivity increase of the rapidly proceeding flocculation reactions perceptible with the naked eye has been achieved by the use of optical instruments measuring the degree of turbidity, the so-called nephelometers.

Nephelometric determinations of concentrations are specific, rapid and favorable as to the price. These methods measure the light scattered by the precipitated particles of a turbid solution. At first, the intensity of the light scattered by solutions of different but known concentrations is measured and a calibration curve is drawn up and the light scattered by the unknown solution is then measured under the same test conditions.

The measuring instruments used consist of an incoherent source of light, an optical system of slots, a cuvette and a photodetector. These instruments have the disadvantage that the sensitivity of detection is often insufficient and the reproducibility of the measuring values at the lower limit is poor.

Moreover, these analytical instruments are very expensive. Automatic devices are used now and then in large hospitals where a great number of samples has to be analyzed. When changing to the determination of another antigen, the device has to be cleaned by rinsing several times. For the determination of a plurality of antigens several parallel analytical units are therefore used.

In small hospitals, in medical practices or in scientific laboratories devices are required the operation of which is more flexible and which are less expensive.

It is, therefore, the object of the present invention to find a device which allows of improving considerably the sensitivity of detection and the reproducibility and which is more flexible in its application.

The present invention provides a process for measuring antigen-antibody reactions by mixing the solution of the antigen to be measured with the corresponding antibody, placing the mixture into the beam of a source of light and measuring the light forwardly scattered by said mixture by a photo-detector, which comprises passing laser light through the mixture, measuring with the photodetector exclusively the light that is forwardly scattered and determining its intensity.

The present invention also provides a device for carrying out the above process which comprises a measuring cuvette placed in the optical axis of a measuring system, said measuring system consisting of a laser, at least two diaphragms, a system of lenses and a photodetector between the diaphragms and the system of lenses, and a light trap in the optical axis of the measuring system between the measuring cuvette and the system of lenses, the light trap having a diameter corresponding to 1.1 to 1.7 times the diameter of the laser beam.

By light traps there are understood, for example, means to absorb to deflect the light such as mirrors, prisms, or light conductors.

To improve the effectiveness of the device, means to cut out the scattered light originating from the diaphragms are provided within the system of lenses.

When a mirror is used as light trap (5 of FIG. 1), the intensity can be amplified by a corresponding adjustment with respect to the end faces of the laser or to a mirror mounted between the laser and the measuring cuvette.

The invention will now be described by way of example with reference to the accompanying drawings of which FIG. 1 is a schematic view of a device according to the invention with the trace of the beam;

Figure 1:
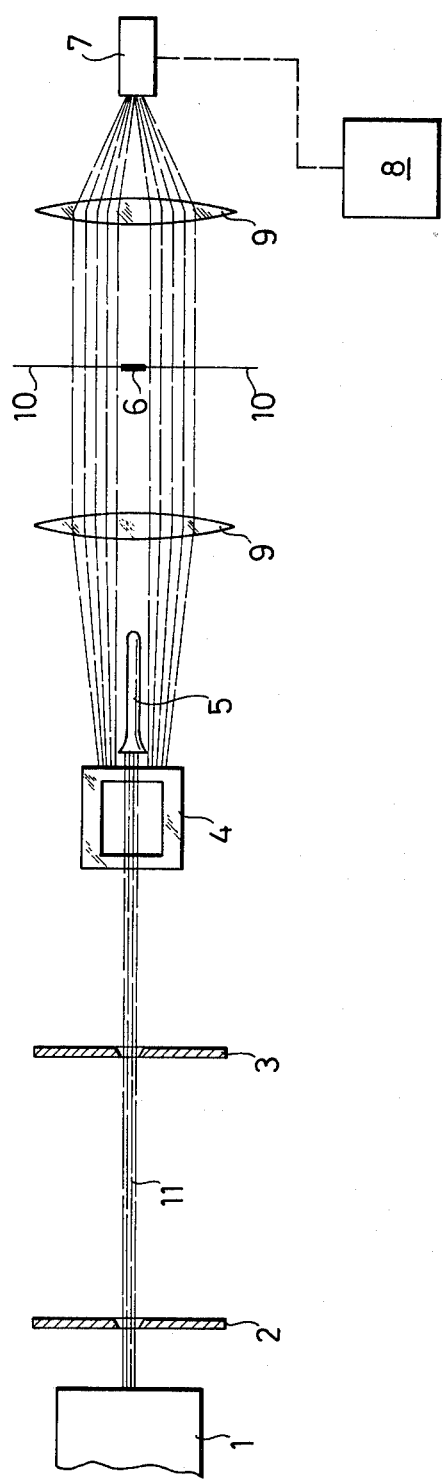

Referring to FIG. 1, two diaphragms 2 and 3 are placed into the beam 11 of a laser 1, for example a He-Ne laser. After having passed the diaphragms, the laser light passes a cuvette 4 having, for example, a depth of 10 mm, a breadth of 4 mm and a height of 20 mm. A unilaterally closed blackened small tube 5 having a diameter of 1.5 mm serves as light trap for the direct laser beam. It is preferably arranged directly behind the cuvette. 0.1 ml of antigen, for example human serum, and 0.1 ml of antiserum containing antibodies against the antigen to be determined are introduced into the cuvette. The precipitate particles formed in the reaction solution scatter the laser light. The light which is scattered in the forward direction is collected with the aid of a system of lenses 9 on a photodetector 7. When the aforesaid cuvette is used, light scattered at a greater angle also passes into the system of lenses by reflexion on the internal walls of the cuvette. The signals of the photodetector 7, for example a photodiode, are passed to a detecting instrument 8, for example a recorder. A small black diaphragm 6 (diameter approximately equal to diameter of laser beam) is suspended on four thin threads 10 within the system of lenses 9. In this manner the scattered light formed at diaphragms 2 and 3 can be cut out and the disturbing background light reduced.

To test the sensitivity and reproducibility of the present process the antigen-antibody reaction of the system albumin/antialbumin was used. As antigen an albumin-containing human blood serum was diluted at a rate of 1 : 52. As antibody an antihuman albumin serum of the canine was used in two dilutions, i.e. 1 : 5 and 1 : 40, respectively. The solutions were filtered through a diaphragm filter preferably having a pore diameter of less than 0.3 μm and equal volumes thereof were charged into the cuvette. After 45 minutes the cuvette was vigorously shaken in order to whirl up the bottom sediments occuring even with low concentrations of less than $10^{-2}$ mg/100 ml. Next, the cuvette was positioned in the laser beam and the scattered light was measured. With a high as well as with a low concentration of antibody a linear relation was found in double logarithmic representation over approximately four powers of ten of the albumin concentration.

Figure 2:
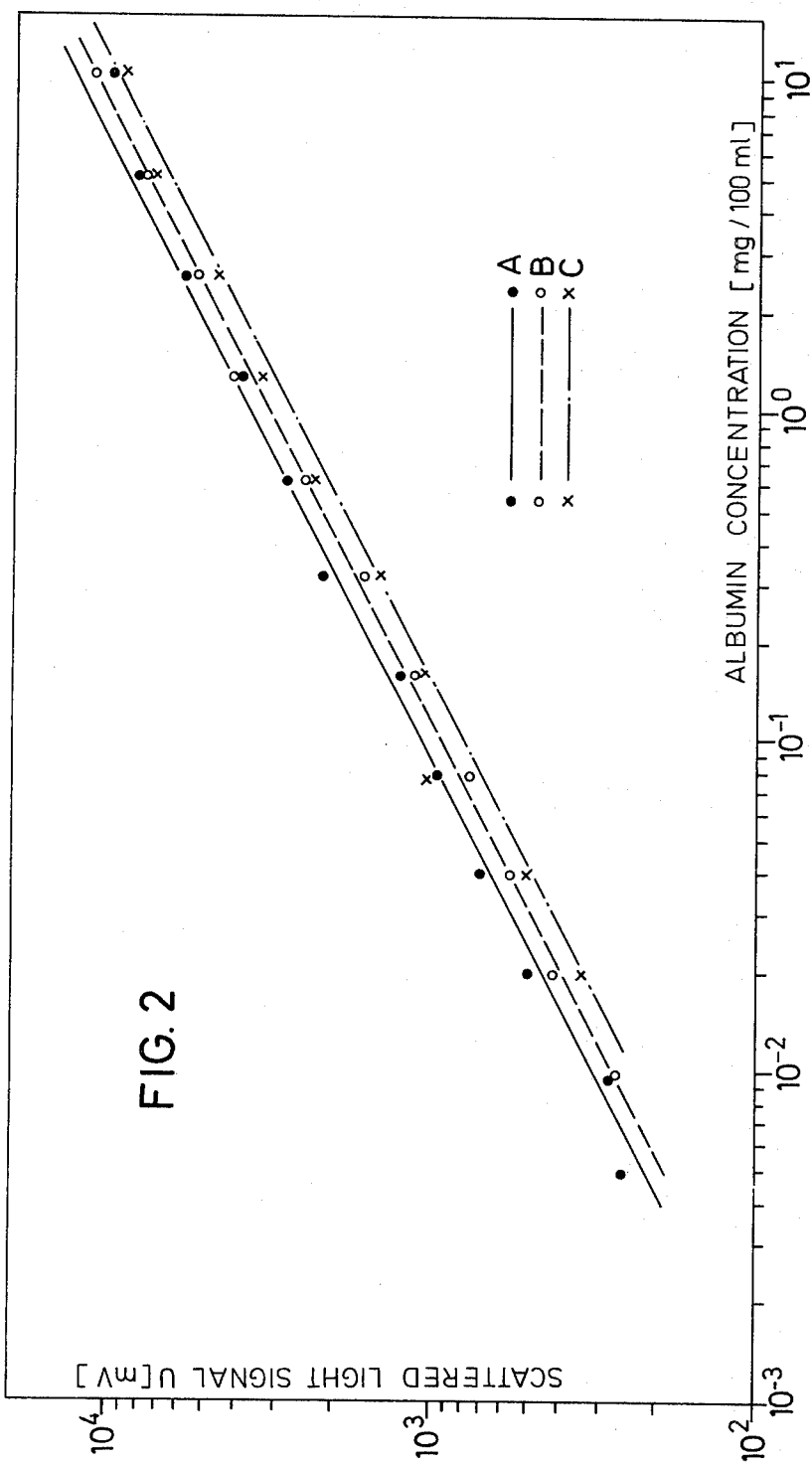
FIG. 2 represent characteristic lines of antigen-antibody reactions.

FIG. 2 shows characteristic lines of antigen-antibody reactions A, B, and C of three different reactions of canine anti-sera with the respective the albumin antigen. The intensity of scattered light U is in linear dependence on the albumin concentration in double logarithmic representation over approximately 4 powers of ten.

The deviations of the measured points from the graphically corrected mean function were only about ± 5 % above a concentration of 0.1 mg/100 ml. With a relatively high concentration of the standard human serum of 10 mg/100 ml the precipitated particles partially dissolved again and the signal of scattered light diminished. In this case, it is recommended to dilute the antigen solution to an appropiate extent.

With conventional measurements of scattered light an accuracy of ± 10 % can be obtained, in the most favorable case the lower limit of detection being approximately $10^{-1}$ mg/100ml. By using a gas laser, for example a He-Ne laser of 1 mW and by measuring the light scattered in forward direction the sensitivity can be increased ten to a hundred times in nephelometric analyses. With the use of very carefully filtered solutions antigen concentrations in the range of from $10^{-2}$ to $10^{-3}$ mg/100 ml $\triangleq$ 0.1 to 0.01 μg/ml can be quantitatively detected. The reproducibility of the measuring point of the calibrating curve is very good.

The device for measuring antigen-antibody reactions can be calibrated and, therefore, it is unnecessary to carry out the hitherto usual control and parallel measurements with calibration substances.

It has also been found that by increasing the efficiency of the source of light three times, for example by replacing a 1 mW laser by a 3 mW laser, and by an improved focusing of the scattered light on the photoelectric receiver, for example by using a microscope lens as lense system 9, the sensitivity of the device according to the invention can be considerably improved. With this more sensitive device measurements in the range of from 0.01 to 0.001 μg/ml become possible and traces of antigens can be detected.

It is known that by adding ethylene glycol the time of the antigen-antibody reaction can be shortened and this fact can also be utilized for the measurements with scattered light from a laser.

Especially when high concentrations of antigens are measured some of the precipitated particles settle out during the reaction period. It is, therefore, necessary vigorously to shake the reaction mixture after completion of the reaction. In general, measured values obtained in this manner can be better reproduced than values of mixtures which have not been shaken.

The process and device according to the invention permit to determine solutions of all antigens against which specific antisera can be obtained. The preferred field of application is, however, the quantitative analysis of the constituents of body fluids, especially of blood plasma, and of antigenic microbial metabolites or plant extracts.

To carry out the process of the invention automatically the device can be modified in a manner analogous to that known for nephelometers with fluorescence spectrophotometer.

The following example illustrates the invention.

EXAMPLE

Figure 3:
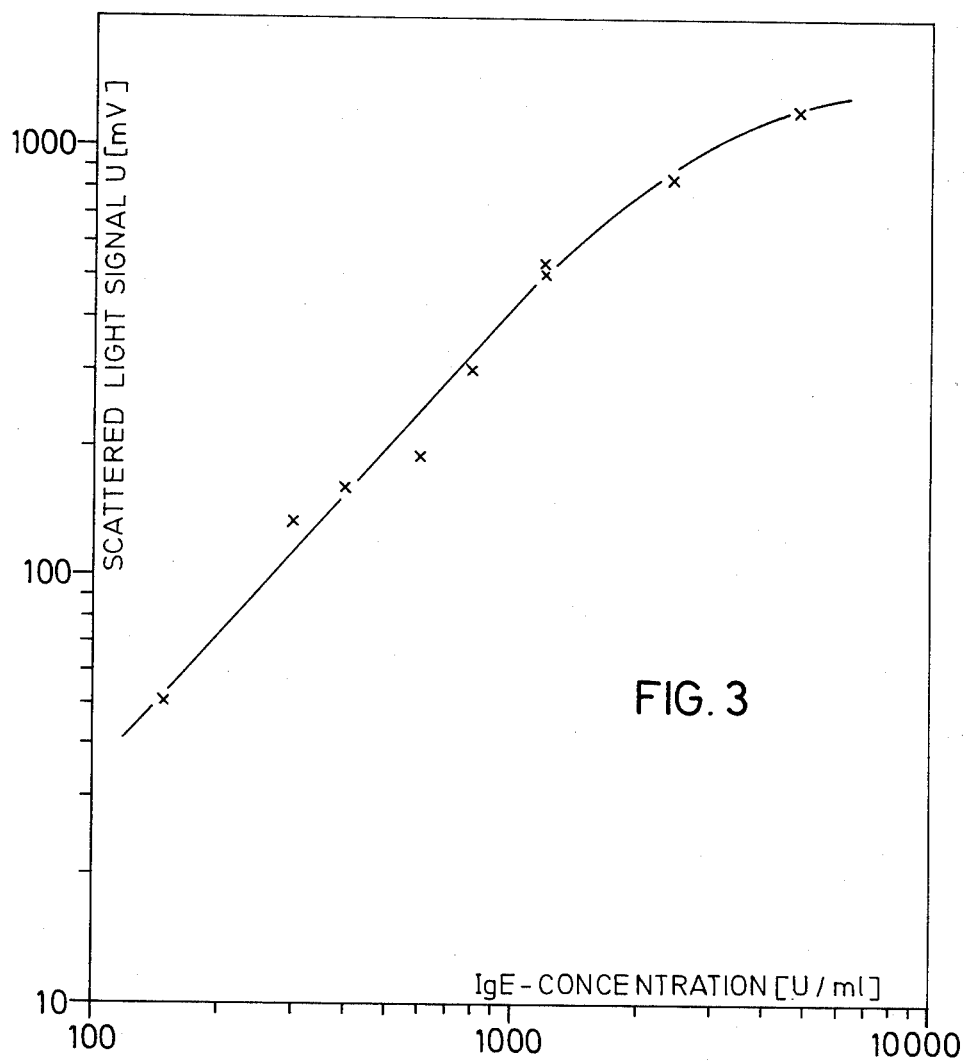
FIG. 3 shows the characteristic curve of immunoglobulin E, in FIGS. 2 and 3 the signal of scattered light U being plotted as a function of the concentration C.

A trace protein in plasma was quantitatively determined. To this effect 2 ml of a serum of a patient were filtered through a diaphragm filter having a pore diameter of 0.05 μm. 0.2 ml of an immunoglobulin E antiserum diluted with isotonic salt solution was introduced into the measuring cuvette of the device and mixed with 0.2 ml of the filtered serum of the patient. The cuvette was closed so as to be airtight and allowed to stand for 16 hours at room temperature. Next, the cuvette was briefly shaken three times. After a time of rest of 10 minutes the cuvette was placed into the ray path of the device measuring the scattered light from the laser. FIG. 3 shows the characteristic line of the immunoglobulin E (IgE)-trace protein obtained by diluting the standard available at the World Health Organization (WHO). The recorded signal U in mV was correlated with the values of the curve and a content of 300 units of IgE/ml was found in the tested serum.

The device according to the invention permits for the first time to determine rapidly and in a simple and very sensitive manner the IgE-protein content in a serum down to a value of 150 units per milliliter. The radial immune diffusion hitherto allowed only a measurement of IgE concentrations above 800 units per milliliter.

What is claimed is:

1. Apparatus for detecting antigen in a liquid by bringing a liquid containing a corresponding antibody into contact therewith to produce a reaction product and measuring the extent to which particles of said reaction product produce light scattering, said apparatus comprising:
   a. a source of laser light,
   b. a pair of spaced diaphragms mounted in front of said source and having apertures aligned with said source to define a parallel ray laser beam having an axis and to intercept undesired radiation,
   c. a sample container adapted to contain a sample of said liquid and positioned in the path of said beam to cause portions of the light of said beam to be scattered by particles of said reaction product,
   d. a photodetector aligned with the axis of said laser beam for measuring the intensity of the scattered light that passes through said sample,
   e. a light converging device located between said sample container and said photodetector for focusing on said photodetector the portion of the beam scattered by the sample, and f. a light trap having a diameter that is 1.1 to 1.7 times the diameter of the undeflected laser beam positioned between said container and said converging device on the axis of said beam to block the undeflected portion of said beam that passes through said container.

2. Apparatus according to claim 1 wherein the light trap consists of a mirror reflecting said undeflected beam into said container.

3. Apparatus according to claim 1 wherein a second light trap having a diameter approximately equal to that of the undeflected laser beam is mounted within the converging device and on the axis of the laser beam.

4. Apparatus according to claim 1 wherein the converging device consists of at least two converging lenses.

* * * * *